United States Patent
Lorentz et al.

(10) Patent No.: US 9,717,660 B2
(45) Date of Patent: Aug. 1, 2017

(54) FLUORIDE RELEASING DENTAL COMPOSITION AND DENTAL APPLIANCE

(71) Applicant: Regents of the University of Minnesota, Minneapolis, MN (US)

(72) Inventors: Katherine L. Lorentz, St. Paul, MN (US); Nathaniel M. Phillips, Eagan, MN (US); Samuel John Schmitz, Brooklyn Center, MN (US); James M. Sieracki, Brooklyn Center, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 48 days.

(21) Appl. No.: 14/633,902

(22) Filed: Feb. 27, 2015

(65) Prior Publication Data
US 2015/0245983 A1    Sep. 3, 2015

Related U.S. Application Data

(60) Provisional application No. 61/946,446, filed on Feb. 28, 2014.

(51) Int. Cl.
*A61C 7/14*    (2006.01)
*A61C 7/08*    (2006.01)
(Continued)

(52) U.S. Cl.
CPC .................. *A61K 8/21* (2013.01); *A61C 7/08* (2013.01); *A61C 7/12* (2013.01); *A61C 19/063* (2013.01);
(Continued)

(58) Field of Classification Search
None
See application file for complete search history.

(56) References Cited

U.S. PATENT DOCUMENTS 4,044,762 A * 8/1977 Jacobs ............... A61O 5/14
128/861
5,074,786 A * 12/1991 Woodward ........... A61J 7/0092
433/229
(Continued)

FOREIGN PATENT DOCUMENTS

EP    0722709 A1    7/1996
EP    0873107 B1    5/2003
WO    9718792 A1    5/1997

OTHER PUBLICATIONS

"ISO 7405:2008 Dentistry—Evaluation of biocompatibility of medical devices used in dentistry," American National Standard/American Dental Association Standard No. 41, 2008, 42 pp. (Applicant points out that, in accordance with MPEP 609.04(a), the 2008 year of publication is sufficiently earlier than the effective U.S. filing date and any foreign priority date of Feb. 2, 2015 so that the particular month of publication is not in issue.).
(Continued)

*Primary Examiner* — Brian T Gedeon
(74) *Attorney, Agent, or Firm* — Shumaker & Sieffert, P.A.

(57) ABSTRACT

A fluoride-releasing dental composition includes a polymeric compound selected from (meth)acrylate polymers, (meth)acrylate copolymers, ethylene vinyl acetate copolymers, and mixtures and combinations thereof; and a cariostatically effective amount of a fluoride compound. A dental appliance made from the fluoride-releasing dental composition.

11 Claims, 4 Drawing Sheets

(51) Int. Cl.
- A61K 8/21 (2006.01)
- A61K 8/81 (2006.01)
- A61C 19/06 (2006.01)
- A61C 7/12 (2006.01)
- A61Q 11/00 (2006.01)

(52) U.S. Cl.
CPC .......... *A61K 8/8135* (2013.01); *A61K 8/8152* (2013.01); *A61Q 11/00* (2013.01); *A61C 7/141* (2013.01)

(56) References Cited

U.S. PATENT DOCUMENTS

| | | | |
|---|---|---|---|
| 5,085,866 A * | 2/1992 | Cowsar | A61K 9/0063 424/475 |
| 5,705,581 A | 1/1998 | Fife et al. | |
| 5,718,924 A | 2/1998 | Braden et al. | |
| 7,097,449 B2 | 8/2006 | Jessop et al. | |
| 2008/0070182 A1* | 3/2008 | Wyllie | A61C 7/141 433/8 |
| 2010/0111891 A1* | 5/2010 | Albrecht | A61K 31/7004 424/78.1 |
| 2012/0156632 A1* | 6/2012 | Schiller | A61C 19/063 433/10 |

OTHER PUBLICATIONS

"Braces," lawndentalcenter.com, retrieved from http://www.lawndentalcenter.com/braces-chicago.html on Jun. 25, 2015, 1 pp.
"Treatment of White Spot Lesions," Pro Dental CPD, retrieved from http://www.prodentalcpd.com/members/articles/orthodontics/orthodontics/treatment_of_white_spot_lesions on Jun. 25, 2015, 2 pp.
Braden, "How Much Do Braces Really Cost? ," 1Dental.com, retrieved from http://www.-Δ1dental.com/articles/dental-insurance/dental-insurance-how-much-braces-cost on Jun. 25, 2015, 6 pp.
Konrad, "How to Plan For and Handle the Cost of Braces," The New York Times, Health, retrieved from http://www.nytimes.com-/2011/01/22/health/22-patient.html?_r=0, Jan. 21, 2011, 3 pp.
Manski et al., "Dental Use, Expenses, Private Dental Coverage, and Changes, 1996 and 2004," Agency for Healthcare Research and Quality; 2007, MEPS Chartbook No. 17, retrieved from http://www.meps.ahrq.gov/mepsweb/data_files/publications/cb17/cb17.pdf, 2007, 144 pp. (Applicant points out that, in accordance with MPEP 609.04(a), the 2007 year of publication is sufficiently earlier than the effective U.S. filing date and any foreign priority date of Feb. 27, 2015 so that the particular month of publication is not in issue.).
"Victory Series™ Bracket System," 3M Victory Series Orthodontic Brackets, 3M Unitek Orthodontic Solutions, retrieved from http://solutions.3m.com/wps/portal/3M/en_US/orthodontics/Unitek/products/metal/Victory-Series/ on Jun. 25, 2015, 2 pp.
"Standard Test Method for Estimating Acute Oral Toxicity in Rats," Annual Book of ASTM Standards, Section 11, Water and Environmental Technology, vol. 11.05, Biological Effects and Environmental Fate; Biotechnology; Pesticides, ASTM E1163-98, 2002, 6 pp. (Applicant points out that, in accordance with MPEP 609.04(a), the 2002 year of publication is sufficiently earlier than the effective U.S. filing date and any foreign priority date of Feb. 27, 2015 so that the particular month of publication is not in issue.).
"Standard Test Methods for Fluoride Ion in Water," ASTM International, Designation: D1179-10, Jul. 2010, 7 pp.
"Standard Guide for Assessment of Antimicrobial Activity Using a Time-Kill Procedure," ASTM International, Designation: E2315-03, May 2008, 5 pp.

* cited by examiner

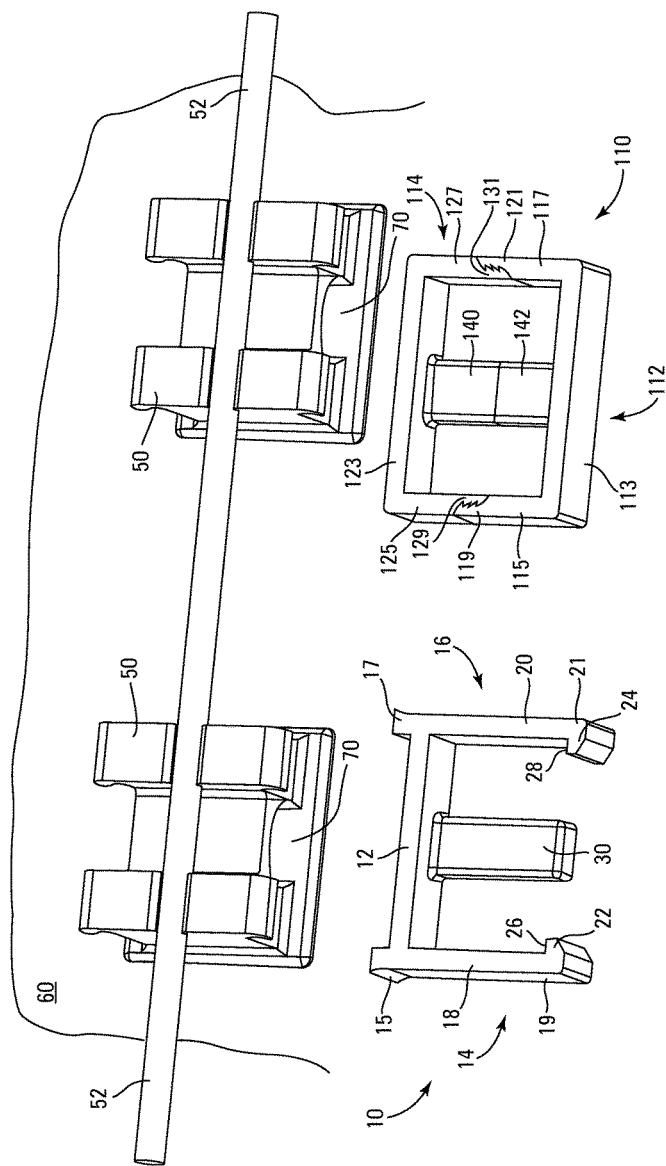

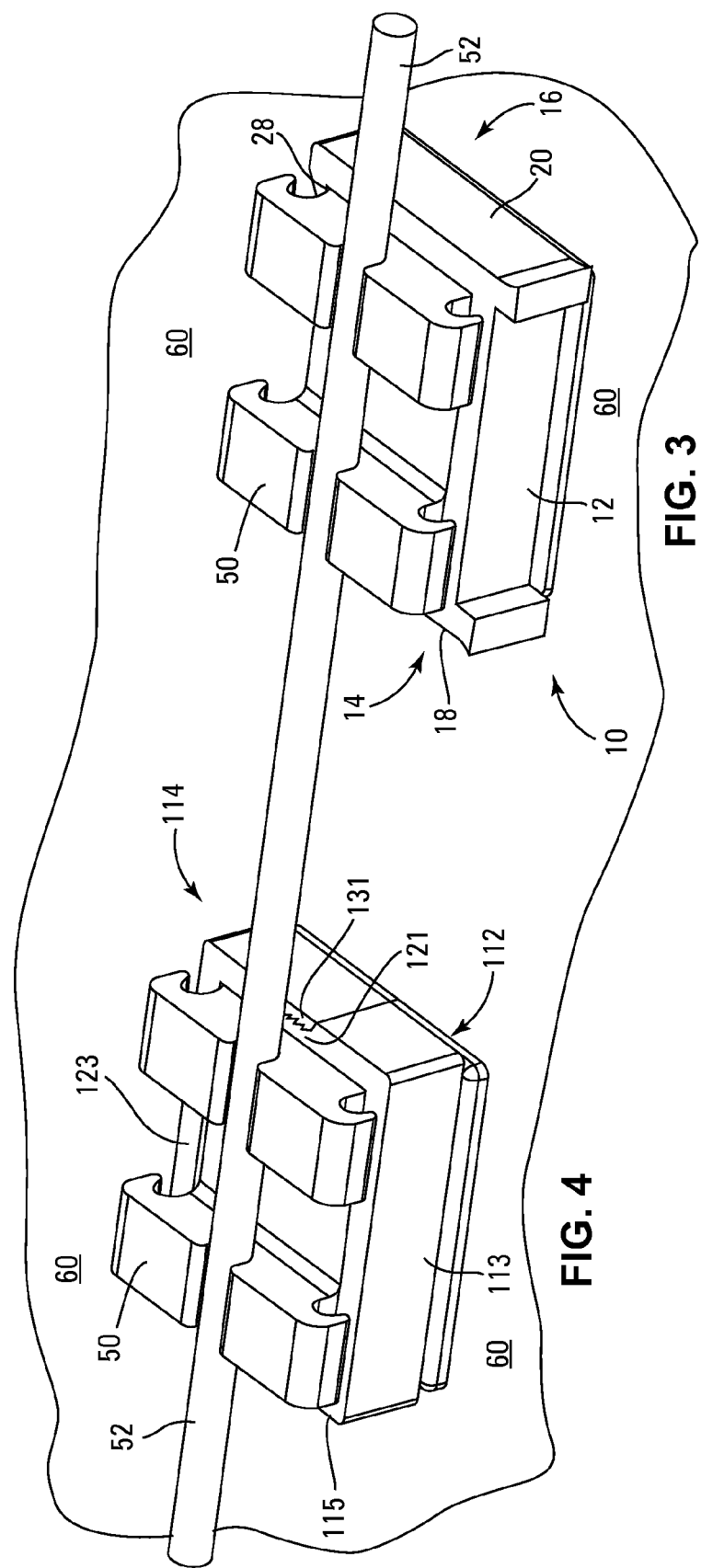

FLUORIDE RELEASING DENTAL COMPOSITION AND DENTAL APPLIANCE

This application claims the benefit of U.S. Provisional Patent Application No. 61/946,446, filed Feb. 28, 2014, the entire contents of which are incorporated herein by reference.

BACKGROUND

The crown, or portion of the tooth exposed from the gums, is completely encased in a layer of enamel, which provides the tooth with its hardness and structure. The main component of the complex crystalline lattice forming the material is a calcium phosphate mineral called hydroxyapatite. Saliva has a specific pH allowing for a natural occurrence of demineralization and remineralization, which adds and removes some of the minerals housed in the exposed enamel. This process is usually held in equilibrium under normal physiological conditions. However, some situations can steer the process towards a greater amount of demineralization than remineralization. Demineralization is caused by a drop in pH in the mouth lower than 5.6, which can result from an increase in organic acid produced by oral microorganisms that form a biofilm on the tooth's enamel. Such microorganisms are capable of consuming sugars and carbohydrates left in the mouth after food is consumed and produce acids which lower the pH at the surface of the tooth. This low pH causes demineralization to take over, and more minerals leech from the tooth surface. If left unchecked, weakened enamel, decay, and cavities can form.

Fluoride reacts with hydroxyapatite to form a strong compound that is less prone to acidic attacks. Fluoride has also been shown to remineralize damaged enamel in the early stages of demineralization, as well as prevent further bacteria growth. The biofilm accumulated on the tooth surface is generally removed by good oral hygiene including brushing the teeth with a fluoride-containing toothpaste, flossing, and rising with mouthwash.

Patients with fixed orthodontic braces confront the challenge of attempting to clean the tooth surfaces close to the brace bracket that a toothbrush cannot reach. Poor cleaning close to the bracket can form a biofilm, which in some cases can result in increased decay and white-spot lesioning.

SUMMARY

In one embodiment, the present disclosure relates to a cariostatic, fluoride-releasing dental composition. In this disclosure, the term cariostatic means a composition that tends to inhibit the formation of dental cavities. The cariostatic dental composition can inhibit, prevent, and/or reverse dental demineralization, which in this disclosure refers to abnormal loss of mineral salts from the surface of a tooth.

In another embodiment, the present disclosure relates to a cariostatic dental appliance made from a fluoride-releasing dental composition. When exposed to the liquid environment of the mouth, i.e. saliva, fluoride ions diffuse from the dental appliance into the surrounding oral environment, and in some embodiments can reduce the amount of bacteria on the surface of the teeth and reduce biofilm accumulation, which in turn can reduce the formation of white spot lesions on the surface of the teeth.

In one embodiment, the present disclosure is directed to a fluoride-releasing dental composition, including a polymeric compound selected from (meth)acrylate polymers, (meth)acrylate copolymers, ethylene vinyl acetate copolymers, and mixtures and combinations thereof; and a cariostatically effective amount of a fluoride compound.

In another embodiment, the present disclosure is directed to a method for making a dental composition, including: (a) mixing a polymeric compound selected from (meth)acrylate polymers, (meth)acrylate copolymers, ethylene vinyl acetate copolymers, and mixtures and combinations thereof; and about 5 wt % to about 60 wt % of a compound; (b) heating the mixture of step (a) to about 350° C.; and (c) injecting the heated mixture of step (b) into a mold to form a dental appliance.

In yet another embodiment, the present disclosure is directed to a fluoride-releasing dental appliance, including a linear central supporting member having at its ends first and second elongate retaining members, wherein the first and the second retaining members each have a first end attached to the central supporting member and extend in a direction normal to a longitudinal axis of the central supporting member, and wherein the second ends of the first and the second retaining members include an engagement flange configured to engage and/or lock on to an orthodontic bracket mounted on a surface of a tooth.

In yet another embodiment, the present disclosure is directed a fluoride-releasing dental appliance, including a pair of opposed U-shaped members, wherein each U-shaped members has a central supporting member and a pair of arms, and wherein the arms include locking members.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 1 is a schematic illustration of an embodiment of a dental appliance made from a fluoride releasing material.

FIG. 2 is a schematic illustration of another embodiment of a dental appliance made from a fluoride releasing material.

FIG. 3 is a schematic illustration of the dental appliance of FIG. 1 mounted on an orthodontic bracket.

FIG. 4 is a schematic illustration of the dental appliance of FIG. 2 mounted on an orthodontic bracket.

DETAILED DESCRIPTION

Figure 5:
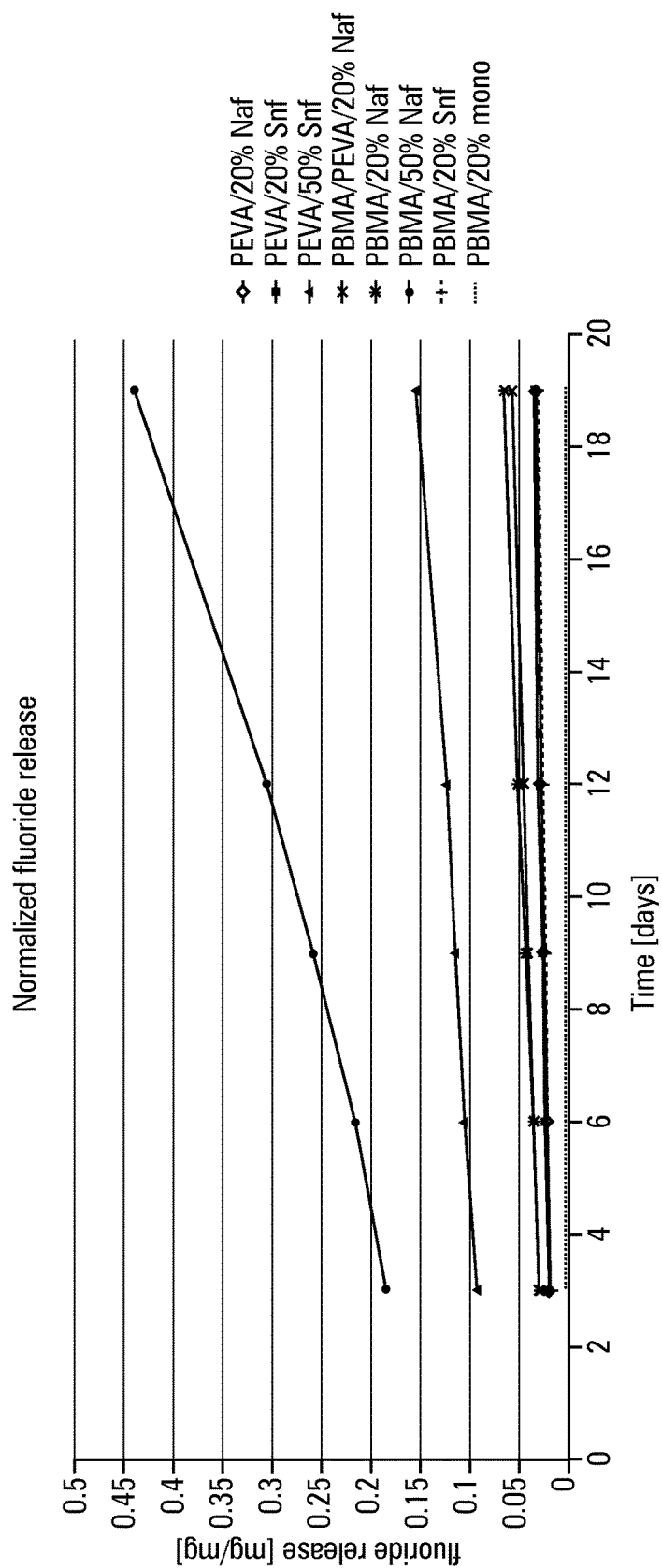
FIG. 5 is a plot of normalized fluoride release vs. time for the dental composition samples of Examples 1-2.

In one aspect, the present disclosure relates to cariostatic dental compositions including at least one polymeric component and a cariostatically effective amount of a non-toxic, biologically acceptable fluoride compound. The cariostatic dental composition of this disclosure can also reduce and/or prevent the formation of biofilms on teeth, which can substantially reduce, prevent demineralization of teeth and formation of white-spot lesions.

The polymeric components of the cariostatic dental compositions of this disclosure are compounds derived from monomers, oligomers, or polymers containing a polymerizable group. Any type of polymer may be used, as long as it is non-toxic and capable of releasing fluoride at a desired rate.

In one embodiment, suitable materials that can provide the polymeric component are the esters of acrylic or methacrylic acid. Examples of these compounds are methyl acrylate, methyl methacrylate, ethyl acrylate, ethyl methacrylate, propyl acrylate, propyl methacrylate, butyl acrylate, butyl methacrylate, isopropyl acrylate, isopropyl methacrylate, 2-hydroxyethyl acrylate, 2-hydroxyethyl methacrylate ("HEMA"), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("BisGMA"), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units varies from 2 to 30), polyethyleneglycol dimethacrylate [where the number of repeating ethylene oxide units varies from 2 to 30, especially triethylene glycol dimethacrylate ("TEGDMA")], neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzenedicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-ethacryloxyethyltrimethyl-hexamethylene dicarbamate, di-1-methyl-2-methacryloxyethyl-dimethylbenzene dicarbamate, di-1-methyl-2-methacryloxyethyldimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyldimethylbenzene dicarbamate, di-1-chloromethyl-2-methacryloxyethyldimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyltrimethylhexamethylenedicarbamate, di-1-methyl-2-methacryloxyethyldimethylbenzene dicarbamate, di-1-methyl-2-methacryloxyethyldimethylcyclohexane dicarbamate, methylene-bis-1-methyl-2-methacryloxyethyl-4-cyclohexyl carbamate, di-b 1-chloromethyl-2-ethacryloxyethyl-hexamethylene dicarbamate, di-1-chloromethyl-2-methacryloxyethyl-trimethylhexamethylene dicarbamate, di-1-chloromethyl-2-methacryloxyethyldimethylbenzene dicarbamate, di-1-chloromethyl-2-methacryloxyethyldimethylcyclohexane dicarbamate, methylene-bis-1-chloromethyl-2-methacryloxyethyl-4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxyphenyl)]propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, 2,2'-bis[3(4-phenoxy)-2-hydroxypropane-1-acryalte]propane, and the like.

In some embodiments, the polymeric component is an acrylate polymer, an acrylate copolymer, a methacrylate polymer, a methacrylate copolymer, and mixtures thereof, which are referred to herein generally as (meth)acrylate polymers and copolymers. In some embodiments, the methacrylate copolymer is poly(butyl methacrylate).

In another embodiment, the polymeric component is a copolymer of ethylene and vinyl acetate (PEVA). In various embodiments, the PEVA copolymer includes about 5 wt % to about 45 wt %, or about 10 wt % to about 40 wt %, or about 9 wt % to about 40 wt %, of the vinyl acetate, with the remainder being ethylene.

Mixtures of the polymeric components are also contemplated. In some embodiments, the polymeric components may be mixed to control material properties of the dental composition or a dental device made therefrom, such as, for example, hardness, hydrophilicity, rate of fluoride release, storage stability, tensile strength, elasticity and the like.

The cariostatic dental composition of this disclosure further includes at least one non-toxic, biologically acceptable fluoride compound. In various embodiments, the fluoride compound may be naturally occurring or synthetic fluoride minerals, fluoride glass such as fluoroaluminosilicate glass, simple and complex inorganic fluoride salts, simple and complex organic fluoride salts or combinations thereof. In various embodiments, the fluoride compound may be selected from metal fluorides that are nontoxic and biologically acceptable such as, for example, sodium fluoride, potassium fluoride, tin fluoride, calcium fluoride, zinc fluoride, bismuth fluoride, $Na_2PFO_3$, and mixtures and combinations thereof.

The fluoride compound should be present in the cariostatic dental composition in a cariostatically effective amount, which is this application means an amount sufficient to provide a clinical cariostatic effect. In various embodiments, a clinical cariostatic effect can include, for example, prevention of the formation of dental cavities, or inhibition, prevention, and/or reversal of dental demineralization. In various embodiments, which are not intended to be limiting, the amount of the fluoride compound present in the cariostatic dental composition can vary from about 1 wt % to about 99 wt %, based on the total weight of the composition, or from about 2 wt % to about 60 wt %, or about 5 wt % to about 50 wt %, or about 10 wt % to about 40 wt %.

In various embodiments, the fluoride compound is present in an amount sufficient to provide a sustained fluoride release into a buffer solution of phosphate buffered saline (PBS) of about 0.05 mg to about 0.5 mg of fluoride per mg of the composition over a period of at least about 20 days. In some embodiments, the fluoride compound is present in the dental composition an amount sufficient to provide a release into a buffer solution of about 0.15 mg to about 0.45 mg fluoride per mg of the composition after the composition has been stored in the buffer solution for about 20 days.

In some embodiments, the dental composition includes optional crosslinkers or initiators or other reactive materials as necessary to form a polymer matrix that retains the fluoride compound.

In various embodiments, the cariostatic dental composition can optionally include additives and fillers that are non-toxic and suitable for use in the mouth. For example, suitable fillers may include, but are not limited to, inorganic materials such as quartz, nitrides (e.g., silicon nitride), glasses derived from, for example Ce, Sb, Sn, Zr, Sr, Ba and Al, colloidal silica, feldspar, borosilicate glass, kaolin, talc, titania, and zinc glass; silica particles and the like. Other suitable additives include, but are not limited to, adjuvants such as cosolvents, pigments, inhibitors, accelerators, viscosity modifiers, surfactants, rheology modifiers, colorants, medicaments and the like.

In some embodiments, dental compositions are made by mixing finely divided particles of the fluoride compound with particles or pellets of the polymeric component(s), along with any optional additives. These components may then be melted, heated in a solvent, or mixed and melted in an extruder.

In some embodiments, the liquid dental composition may then be cooled or injection molded to form a dental appliance. In such cases the cured or hardened polymer should be sufficiently stiff and elastic to allow attachment to a dental bracket on a tooth. In various embodiments, the dental appliance should not degrade in the mouth of a patient for a period of at least about 4 weeks, or at least about 6 weeks, or at least about 12 weeks, or longer.

The cariostatic dental compositions described herein can be used in a variety of applications in the dental or medical fields in which a material is desired that will provide a sustained release of fluoride. For example, in some orthodontic procedures, metal wires are inserted into stainless steel or ceramic orthodontic brackets that are affixed to the teeth. The wires interact with the brackets to move teeth into a desired position. In some embodiments, the dental compositions can be coated on metal or ceramic dental appliances. In other embodiments, the dental compositions can be molded into dental appliances that can be attached to or mounted on the orthodontic brackets to provide a sustained release of fluoride onto the teeth during orthodontic treatment. In other embodiments, the dental compositions may be molded into, incorporated into, or coated on mouthguards, retainers, aligners or other polymeric materials intended to move teeth or maintain dental alignment such as, for example, the molded retainers available under the trade designation Invisalign from Align Technology, Inc., San Jose, Calif.

FIG. 1 is a schematic illustration of an embodiment of a dental appliance 10 molded from a fluoride-releasing dental composition, which in some non-limiting embodiments can be the cariostatic dental composition described above. The dental appliance 10 includes a linear central supporting member 12 having at its ends two opposed retaining members 14 and 16. The retaining members 14, 16 have a first end 15, 17 attached to the central supporting member. Each retaining member 14, 16 includes an elongate portion 18, 20 that extends in a direction substantially normal to a longitudinal axis of the central supporting member 12. A second end 19 of the retaining member 14 includes a flange 22 that extends normal to a longitudinal axis of the elongate portion 18 and toward the elongate portion 20 of the retaining member 16. A second end 21 of the retaining member 16 includes a flange 24 that extends normal to a longitudinal axis of the elongate portion 20 thereof and toward the elongate portion 18 of the retaining member 14. The flanges 22, 24 include shoulders 26, 28 shaped to engage and/or lock on to an orthodontic bracket 50 mounted on a surface 60 of the tooth of a patient.

To more securely mount the dental appliance 10 to the bracket 50, the appliance 10 may optionally further include an elongate, linear tongue member 30 shaped to engage an aperture 70 in the bracket 50. In this embodiment, the tongue member 30 is attached to the central supporting member 12 in a position midway between the first ends 15 and 17 of the retaining members 14, 16, and extends in a direction parallel to the longitudinal axes of the retaining members 14, 16.

As shown in FIG. 3, the dental appliance 10 can be mounted onto the orthodontic bracket 50 in a region between the metal wire 52 and the tooth surface 60 such that the shoulders 26, 28 engage the bracket 50 and lock the appliance 10 into position. The tongue member 30 is inserted into the aperture 70 in the bracket 50 (not shown in FIG. 3) to more securely mount the dental appliance 10 and maintain its position on the bracket 50. Once so mounted, the dental appliance 10 continuously releases fluoride onto the tooth surface 60 to reduce and/or eliminate the occurrence of biofilms and white spot lesions on the tooth adjacent to the orthodontic bracket 50.

Referring to FIG. 2, another embodiment of the dental appliance 110 made from a fluoride-releasing material includes opposed U-shaped members 112, 114. The U-shaped member 112 includes a central supporting member 113 and arms 115, 117. The arms 115, 117 include locking members 119, 121. The U-shaped member 114 includes a central supporting member 123, and arms 125, 127. The arms 125, 127 include locking members 129, 131 with engaging teeth.

The U-shaped members 112, 114 further optionally include opposed linear tongue members 140, 142 that in some embodiments can include locking members thereon (not shown in FIG. 2). The tongue members 140, 142 are sized to engage an aperture 70 in an orthodontic bracket 50.

As shown in FIG. 4, the dental appliance 110 can be mounted onto the orthodontic bracket 50 in a region between the metal wire 52 and the tooth surface 60 such that the U-shaped members 112, 114 engage the bracket 50 and lock the appliance 110 into position. Teeth on the locking members 121, 131 (and 119, 129) on the U-shaped members 114, 112 engage and lock appliance 110 onto the bracket 50. The opposed tongue members 140, 142 are inserted into the aperture 70 in the bracket 50 (not shown in FIG. 4) to more securely mount the dental appliance 110 and maintain its position on the bracket 50. the Once so mounted, the dental appliance 110 continuously releases fluoride onto the tooth surface 60 to reduce and/or eliminate the occurrence of biofilms and white spot lesions on the tooth adjacent to the orthodontic bracket 50.

The present invention will be further understood in view of the following examples, which are merely illustrative and not meant to limit the scope of the invention.

EXAMPLES

Example 1

Polymer batches were created using both solvent and melting methods.

Sodium Fluoride (NaF) was used in combination with different polymers as shown in Table 1 below: Poly(ethylene-co-vinyl acetate) (PEVA), Poly(butyl methacrylate) (PBMA), and Gelatin.

TABLE 1

| Method | Fluoride Releasing Composition | Fluoride Releasing Composition |
| --- | --- | --- |
| Solvent | NaF 5 wt % | NaF 20 wt % |
| Solvent | PEVA 40% | PEVA 40% |
| Solvent | PEVA 9% | PEVA 9% |
| Solvent | PBMA | PBMA |
| Solvent | Gelatin | Gelatin |
| Melt | PEVA 40% | PEVA 40% |

Example 2

The compositions shown in Table 2 below were mixed in a Rheomix 600 mixer and prepared in a Thermo Electron Polylab extruder.

TABLE 2

| Fluoride Compound | Polymer PEVA 40% | Polymer 1:1 wt % PEVA:PBMA | Polymer PBMA |
|---|---|---|---|
| NaF 20 wt % | X | X | X |
| NaF 50 wt % | — | — | X |
| SnF 20 wt % | X | — | X |
| SnF 50 wt % | X | — | X |
| $Na_2PFO_3$ 20 wt % | — | — | X |

Example 3

All samples from Examples 1-2 above were soaked in 10 mL PBS buffer solution for a period of three days, then removed and transferred to the next vial. Fluoride concentration measurements were taken using a commercially available fluoride meter.

The results are shown in FIG. 5, which is a plot of the release profiles for each polymer tested in the form of percent fluoride released vs. time. It can be seen that the PBMA (50% NaF) had the most desirable release profile, having the capability to not only release the greatest amount of fluoride, but also over a duration that agreed with clinical research. It can also be estimated that if testing continued, the release profile would continue to leech fluoride over the duration of the brackets' presence in the patient.

Example 4

Figure 6:
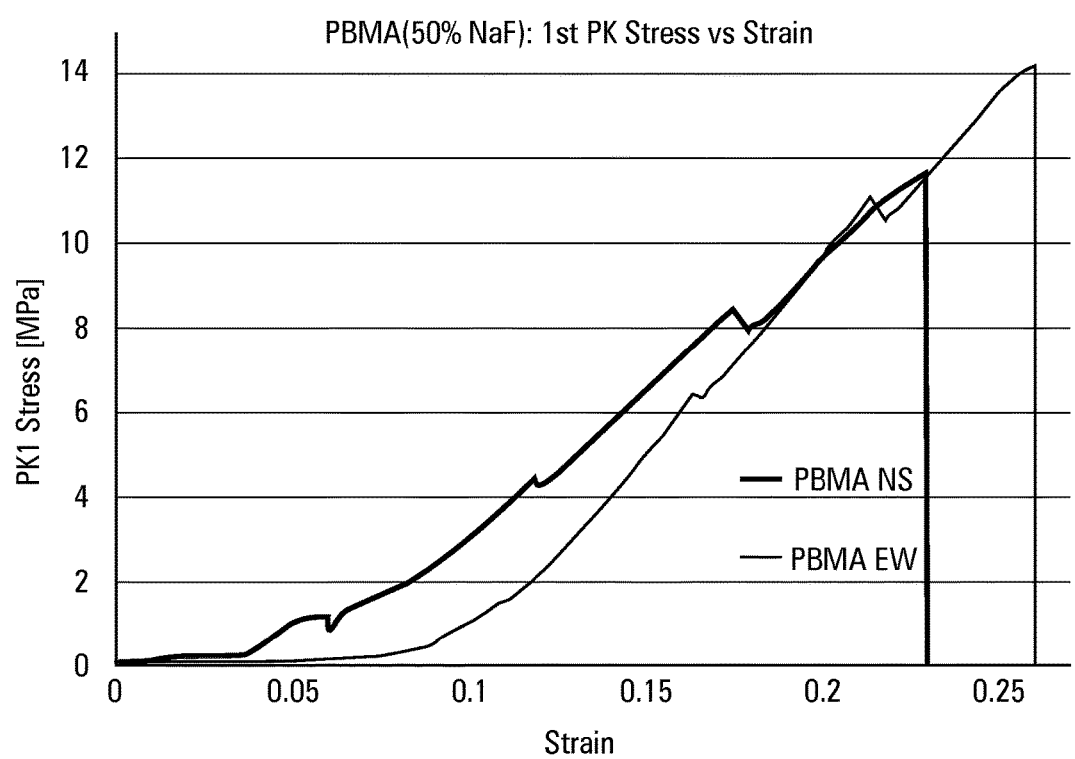
FIG. 6 is a plot of the stress vs. strain for the dental composition made from the sample PBMA (50 wt % NaF) from Example 2.

Uniaxial tensile testing was done in two directions to obtain the mechanical properties of the PBMA (50 wt % NaF) sample, and the resulting stress vs. strain is plotted in FIG. 6. These values were used to perform finite element analysis. From this, we concluded the clip as tested was structurally capable of deforming enough to be put on and taken off.

Various embodiments of the invention have been described. These and other embodiments are within the scope of the following claims.

The invention claimed is:

1. A fluoride-releasing dental composition, comprising:
a polymeric compound chosen from butyl methacrylate, ethylene vinyl acetate, and mixtures and combinations thereof; and
about 50 wt% of a fluoride compound chosen from NaF, SnF, and mixtures and combinations thereof.

2. The dental composition of claim 1, wherein the polymeric compound is butyl methacrylate.

3. The dental composition of claim 1, wherein the dental composition comprises butyl methacrylate and about 50 wt % NaF.

4. The dental composition of claim 2, wherein the dental composition releases about 0.15 mg to about 0.45 mg fluoride per mg of the composition after continuous storage in a buffer solution for 20 days.

5. A method for making a dental appliance, comprising:
(a) mixing a polymeric compound chosen from (meth)acrylate polymers, (meth)acrylate copolymers, ethylene vinyl acetate copolymers, and mixtures and combinations thereof,
about 20 wt % to about 50 wt % of a fluoride compound chosen from NaF, SnF, $Na_2PFO_3$, and mixtures and combinations thereof;
(b) heating the mixture of step (a) to about 350° C.; and
(c) injecting the heated mixture of step (b) into a mold to form a dental appliance.

6. A dental appliance formed from the fluoride-releasing dental composition of claim 1.

7. The dental appliance of claim 6, wherein the dental appliance comprises a tooth alignment tray.

8. A fluoride-releasing dental appliance, comprising:
a linear central supporting member having at its ends first and second elongate retaining members, wherein the first and the second retaining members each have a first end attached to the central supporting member and extend in a direction normal to a longitudinal axis of the central supporting member, and wherein the second ends of the first and the second retaining members comprise an engagement flange configured to engage and/or lock on to an orthodontic bracket mounted on a surface of a tooth,
an elongate, linear tongue attached to the central supporting member midway between the first and the second retaining members, wherein the linear tongue extends in a direction parallel to a longitudinal axis of the first and the second retaining members, and wherein the linear tongue is configured to engage an aperture in the orthodontic bracket, and
wherein the appliance is formed from a fluoride releasing dental composition comprising:
a polymeric compound chosen from (meth)acrylate polymers, (meth)acrylate copolymers, ethylene vinyl acetate copolymers, and mixtures and combinations thereof; and
about 20 wt % to about 50 wt % of a fluoride compound chosen from NaF, SnF, $Na_2PFO_3$, and mixtures and combinations thereof.

9. An orthodontic bracket having attached thereto the dental appliance of claim 8.

10. A fluoride-releasing dental appliance, comprising:
a pair of opposed U-shaped mating members, wherein each U-shaped member comprises a central supporting member and a pair of arms, and wherein the arms comprise locking ratcheting teeth,
wherein each U-shaped member comprises a linear tongue member attached to the central support member between the pair of arms and extending in a direction parallel to a longitudinal axis of the arms, wherein the linear tongue members are configured to engage an aperture in an orthodontic bracket, and
wherein the U-shaped members and tongue members are formed from a fluoride-releasing polymeric compound chosen from (meth)acrylate polymers, (meth)acrylate copolymers, ethylene vinyl acetate copolymers, and mixtures and combinations thereof, and about 20 wt % to about 50 wt % of a fluoride compound chosen from NaF, SnF, $Na_2PFO_3$, and mixtures and combinations thereof.

11. An orthodontic bracket having attached thereto the dental appliance of claim 10.

* * * * *